United States Patent
Jusiak et al.

(10) Patent No.: US 9,066,794 B2
(45) Date of Patent: Jun. 30, 2015

(54) PATIENT/INVALID SUPPORT

(71) Applicants: Joel T. Jusiak, Holland, NY (US);
Patrick Lafleche, Kalamazoo, MI (US);
Joseph M. Zabawa, Buffalo, NY (US)

(72) Inventors: Joel T. Jusiak, Holland, NY (US);
Patrick Lafleche, Kalamazoo, MI (US);
Joseph M. Zabawa, Buffalo, NY (US)

(73) Assignee: Stryker Corporation, Kalamazoo, MI (US)

(*) Notice: Subject to any disclaimer, the term of this patent is extended or adjusted under 35 U.S.C. 154(b) by 0 days.

(21) Appl. No.: 13/623,910

(22) Filed: Sep. 21, 2012

(65) Prior Publication Data

US 2013/0067662 A1 Mar. 21, 2013

Related U.S. Application Data

(60) Provisional application No. 61/537,325, filed on Sep. 21, 2011.

(51) Int. Cl.
| | |
|---|---|
| *A47C 17/86* | (2006.01) |
| *A61F 7/08* | (2006.01) |
| *B32B 3/26* | (2006.01) |
| *A61G 7/057* | (2006.01) |
| *A61F 7/00* | (2006.01) |

(52) U.S. Cl.
CPC ... *A61F 7/08* (2013.01); *B32B 3/26* (2013.01); *A61G 7/05715* (2013.01); *A61G 7/05738* (2013.01); *A61G 7/05769* (2013.01); *A61G 2007/05792* (2013.01); *A61G 2210/70* (2013.01); *A61G 2210/90* (2013.01); *A61F 2007/0064* (2013.01)

(58) Field of Classification Search
CPC ....................................... A47C 17/86
USPC .................. 5/726–727, 714, 722, 652.1–2
See application file for complete search history.

(56) References Cited

U.S. PATENT DOCUMENTS

| | | | |
|---|---|---|---|
| 3,485,787 A | 12/1969 | Haefele et al. | |
| 3,676,387 A | 7/1972 | Lindlof | |
| 3,827,999 A | 8/1974 | Crossland | |
| 4,259,540 A | 3/1981 | Sabia | |
| 4,351,913 A | 9/1982 | Patel | |
| 4,369,284 A | 1/1983 | Chen | |
| 4,432,607 A | 2/1984 | Levy | |
| 4,492,428 A | 1/1985 | Levy | |
| 4,497,538 A | 2/1985 | Patel | |
| 4,509,821 A | 4/1985 | Stenger | |
| 4,618,213 A | 10/1986 | Chen | |
| 4,709,982 A | 12/1987 | Corne et al. | |

(Continued)

FOREIGN PATENT DOCUMENTS

WO 2010078047 7/2010

OTHER PUBLICATIONS

PCT International Search Report, dated Dec. 18, 2012, for International Application No. PCT/US2012/056457.

(Continued)

*Primary Examiner* — Fredrick Conley
(74) *Attorney, Agent, or Firm* — Warner Norcross & Judd LLP

(57) ABSTRACT

A patient support includes a gel-based cushioning layer and an air distribution manifold located beneath the cushioning layer. The cushioning layer includes a plurality of transverse passageways extending therethrough to allow airflow through the cushioning layer and to the patient interface with the cushioning layer.

16 Claims, 4 Drawing Sheets

(56) References Cited

U.S. PATENT DOCUMENTS

| | | |
|---|---|---|
| 4,716,183 A | 12/1987 | Gamarra et al. |
| 4,798,853 A | 1/1989 | Handlin, Jr. |
| 4,942,270 A | 7/1990 | Gamarra |
| 5,107,558 A * | 4/1992 | Luck ............... 5/727 |
| 5,149,736 A | 9/1992 | Gamarra |
| 5,239,723 A | 8/1993 | Chen |
| 5,262,468 A | 11/1993 | Chen |
| 5,325,551 A | 7/1994 | Tappel et al. |
| 5,331,036 A | 7/1994 | Kang et al. |
| 5,334,646 A | 8/1994 | Chen |
| 5,336,708 A | 8/1994 | Chen |
| 5,475,890 A | 12/1995 | Chen |
| 5,508,334 A | 4/1996 | Chen |
| 5,542,136 A | 8/1996 | Tappel |
| 5,749,111 A | 5/1998 | Pearce |
| 5,881,409 A | 3/1999 | Pearce |
| 5,994,450 A | 11/1999 | Pearce |
| 6,026,527 A | 2/2000 | Pearce |
| 6,197,099 B1 | 3/2001 | Pearce |
| 6,413,458 B1 | 7/2002 | Pearce |
| 6,447,865 B1 | 9/2002 | Flick et al. |
| 6,843,873 B2 | 1/2005 | Flick et al. |
| 6,865,759 B2 | 3/2005 | Pearce |
| 7,060,213 B2 | 6/2006 | Pearce |
| 7,730,566 B2 | 6/2010 | Flick et al. |
| 7,823,233 B2 | 11/2010 | Flick et al. |
| 7,823,234 B2 | 11/2010 | Flick et al. |
| 7,827,636 B2 | 11/2010 | Flick et al. |
| 7,930,782 B2 | 4/2011 | Chen |
| 7,964,664 B2 | 6/2011 | Pearce |
| 8,397,326 B2 | 3/2013 | Lafleche et al. |
| 8,832,885 B2 | 9/2014 | Lafleche et al. |
| 8,856,992 B2 | 10/2014 | Lafleche et al. |
| 8,910,334 B2 | 12/2014 | Lafleche et al. |
| 8,911,387 B2 | 12/2014 | Lafleche et al. |
| 2007/0261548 A1 * | 11/2007 | Vrzalik et al. ............... 95/52 |
| 2007/0277313 A1 * | 12/2007 | Terech ............... 5/421 |
| 2007/0283496 A1 | 12/2007 | Skripps |
| 2010/0071137 A1 | 3/2010 | Doehler et al. |
| 2011/0048429 A1 | 3/2011 | Callahan |

OTHER PUBLICATIONS

PCT Written Opinion, dated Dec. 18, 2012, for International Application No. PCT/US2012/056457.

* cited by examiner

PATIENT/INVALID SUPPORT

The present application claims the benefit of U.S. provisional Application No. 61/537,325, filed Sep. 21, 2011, entitled PATIENT SUPPORT SURFACE WITH LOW AIR LOSS SYSTEM, by Applicant Joel T. Jusiak, which is incorporated by reference herein in its entirety.

TECHNICAL FIELD AND BACKGROUND OF THE INVENTION

The present invention relates to a support and, more particularly, a patient or invalid support, such as a mattress, that is adapted for use on a patient bed used in a hospital or other patient care facilities, including long term care facilities or the like.

When patients are hospitalized or bedridden for any significant amount of time, patients can develop pressure sores or ulcers. These pressure sores or ulcers can be exacerbated by the patient's own poor circulation, such as in the case of diabetic patients, but typically form as a result of prolonged immobility, which allows the pressure exerted on the patient's skin from the mattress to decrease circulation in the patient's tissue. In addition to reducing circulation in the patients' tissue, lack of mobility can also cause moisture build-up at the point of contact with the mattress. Moisture build-up can cause maceration in the skin—which makes the skin more permeable and vulnerable to irritants and stresses, such as stresses caused by pressure or by shear, for example when a patient is moved across a mattress.

Accordingly there is a need for a mattress that can reduce the pressure on a patient's skin and further that can improve air circulation to the patient's skin, all in an attempt to improve the care of a patient.

SUMMARY OF THE INVENTION

The present invention provides a patient support that provides a microclimate management system that improves air circulation at the interface between the patient and the patient support.

In one form of the invention, a patient support includes a gel-based cushioning layer and an air distribution manifold that is located beneath the cushioning layer. The cushioning layer includes a plurality of transverse passageways extending there through to allow air flow through the cushioning layer and to the patient interface with the cushioning layer.

In another form of the invention, a patient support includes a layer of bladders. The bladders each have an upwardly facing surface for facing and supporting the patient. The layer of bladders also includes transverse openings that extend through the layer of bladders from the lower side of the layer to the patient facing side of layer. Located beneath the layer of bladders is an air distribution manifold that is configured and arranged to direct air flow through the layer of bladders.

In one aspect, in any of the above air distribution manifolds, the manifold may comprise an air distribution bladder. For example, the bladder may comprise a first side and a second side spaced from and generally parallel to the first side wherein the bladder has a generally flat or planar configuration.

In a further aspect, the sides of any of the above air distribution bladders are configured to remain in their spaced and generally parallel configuration even when the air distribution bladder is fully inflated. For example, the air distribution bladder optionally includes a porous intermediate, spacer layer that maintains the two sides in their spaced relationship while allowing air to flow through the air distribution bladder. A suitable spacer layer may include a three dimensional (3D) fabric.

According to another aspect, the air distribution bladder's two sides may be interconnected by ties or welds in a plurality of locations across the air distribution bladder so that the air distribution bladder remains generally flat even when inflated.

In yet another aspects, the thickness of the air distribution bladder when inflated is in a range of ¼ inch to 2 inches or in a range of ½ inch to 1¾ inches. Further, the variation in thickness when inflated is less than ½ inch or less than ¼ inch, and optionally less than ⅛ inch.

In yet a further aspect, the air distribution bladders may be formed from at least one sheet of material which is folded over and sealed together at or near its unconnected edges to form an enclosed volume. The upper sheet portion or first side of the air distribution bladder includes a plurality of apertures, which either may be formed in the upper sheet portion or may be provided by interstices in the material forming the upper sheet portion. For example, the upper sheet portion may be a gas permeable material sheet or may include a region of gas permeable material. For example, the sheet may be sealed by welding, such as by heat sealing. Suitable material for the sheets include non-woven materials, such as nylon, including urethane coated nylon, as well as elastic materials, such as Lycra, including a combination of material, such as Lycra and GORTEX.

Accordingly to yet another aspect, the air distribution bladder may be formed from a semi-rigid material, such as a corrugated panel, with the corrugations forming air flow passageways through the bladder. Again, openings may be provided in the upper side of the air distribution bladder, which are in fluid communication with the passageways to allow the air distribution bladders to direct air flow to the patient interface with the cushioning layer.

In any of the above air distribution bladders, the air distribution bladder may extend partially across the width and/or length of the cushioning layer. In addition, the air distribution bladder is secured in the patient support, for example, to a base layer beneath the bladder. For example, one or both ends of the bladder may be anchored.

Further, two or more air distribution bladders may be used.

In addition to the gel-based cushioning layer, the patient support may also include a second cushioning layer. For example, the second cushioning layer may comprise a second gel-based cushioning layer.

In addition, the patient support may further include a foam crib, which supports the cushioning layer, with the bladder optionally located beneath the foam crib.

In another form of the invention, a patient support includes a first cushioning layer and a flexible air distribution layer that is located beneath the cushioning layer. The cushion layer includes a plurality of transverse passageways extending there through to allow air flow through the cushioning layer and to the patient interface with the first cushioning layer.

In one aspect, the patient support includes a second cushioning layer located beneath the first cushioning layer. For example, the flexible air distribution layer may be located beneath the second cushioning layer, with the second cushion layer also including a plurality of transverse passageways extending there through to allow air flow through the cushioning layers and to the patient interface with the first cushioning layer.

In another aspect, at least one of the cushioning layers is a gel-based cushioning layer. In a further aspect, both cushioning layers are gel-based cushioning layers.

According to yet another form of the invention a low air loss bladder includes a flexible upper sheet portion and a flexible lower sheet portion, and a spacer layer between the upper and lower sheet portions to form an air distribution region. The upper sheet portion is adapted to allow air flowing through the air distribution region to flow from the upper sheet portion.

In one aspect, the upper sheet portion includes transverse openings. Additionally, the variation in thickness of the bladder when inflated is less than ½ inch or less than ¼ inch, and optionally less than ⅛ inch.

In another aspect, the upper and lower sheet portions are maintained in a spaced relationship and generally parallel so that the bladder has a generally flat or planar configuration when inflated. For example, each sheet portion may be connected to the spacer layer so that the spacer layer keeps the upper and lower sheet portions in their spaced relationship. A suitable spacer layer may include a three dimensional (3D) fabric. Alternately or in addition, the sheet portions may be connected by ties or by welds formed between the two sheet portions.

Accordingly, the present invention provides a patient support that is configured to increase fluid (e.g. moisture vapor or moisture vapor and air) circulation through the support, which may help to keep the patient cool and dry.

These and other objects, advantages, purposes, and features of the invention will become more apparent from the study of the following description taken in conjunction with the drawings.

DETAILED DESCRIPTION OF THE PREFERRED EMBODIMENTS

Figure 1:
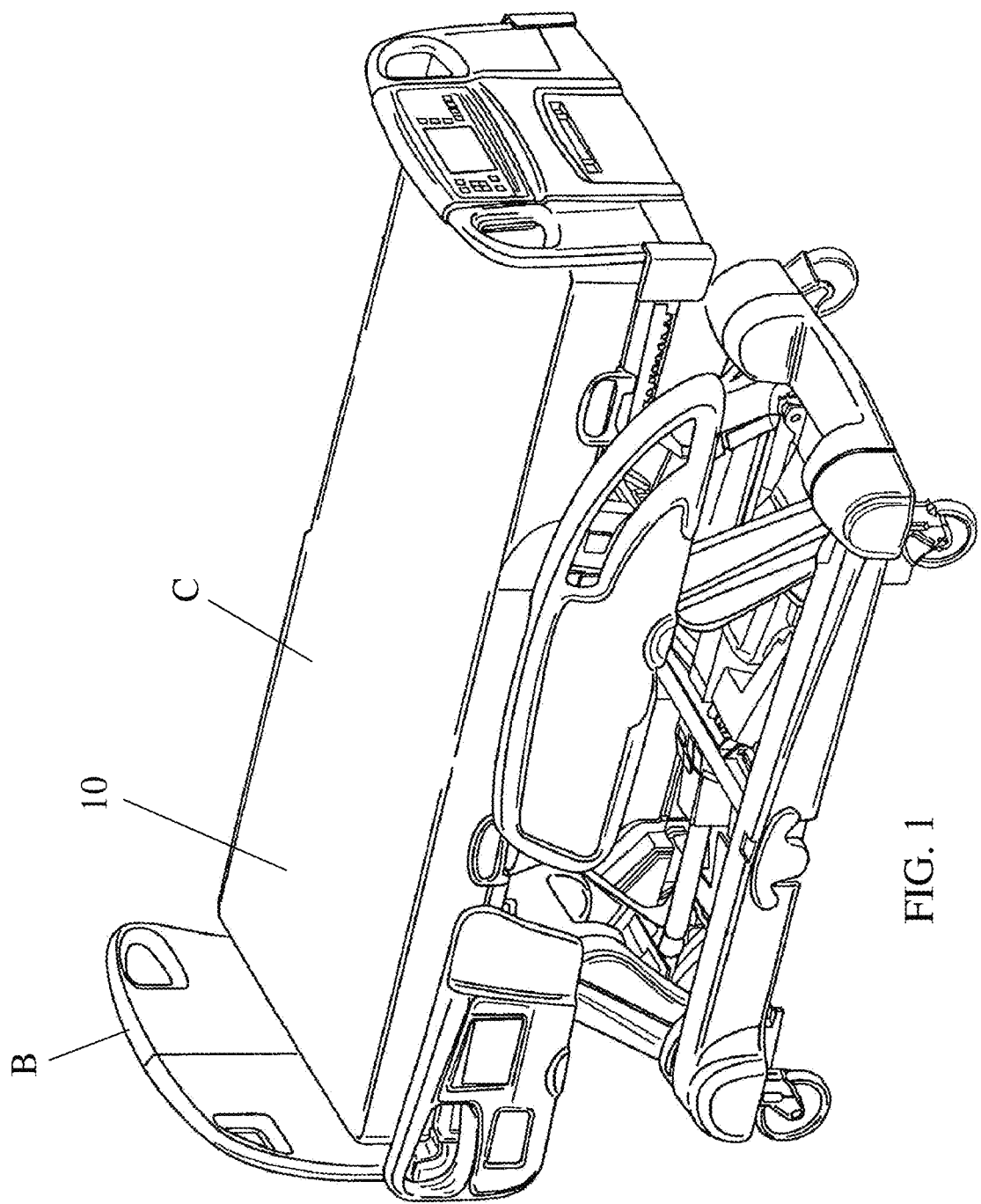
FIG. 1 is a perspective view of a patient support of the present invention supported on a bed.

Referring to FIG. 1, the numeral 10 generally designates a patient support of the present invention. As will be more fully described below, support 10 may be configured as a mattress for a bed B, such as a hospital bed, and comprises a system of layers that together provide increased comfort for the patient and a low air loss system to provide increased air circulation in the support itself to thereby reduce the moisture build up at the interface between the patient and the support. For details of a suitable bed, reference in made herein to the beds described in U.S. Pat. Nos. 8,006,332; 7,690,059; 7,805,784; 7,962,981; and 7,861,334, all commonly owned by Stryker Corporation of Kalamazoo, Mich., which are herein incorporated by reference in their entireties.

Figure 2:
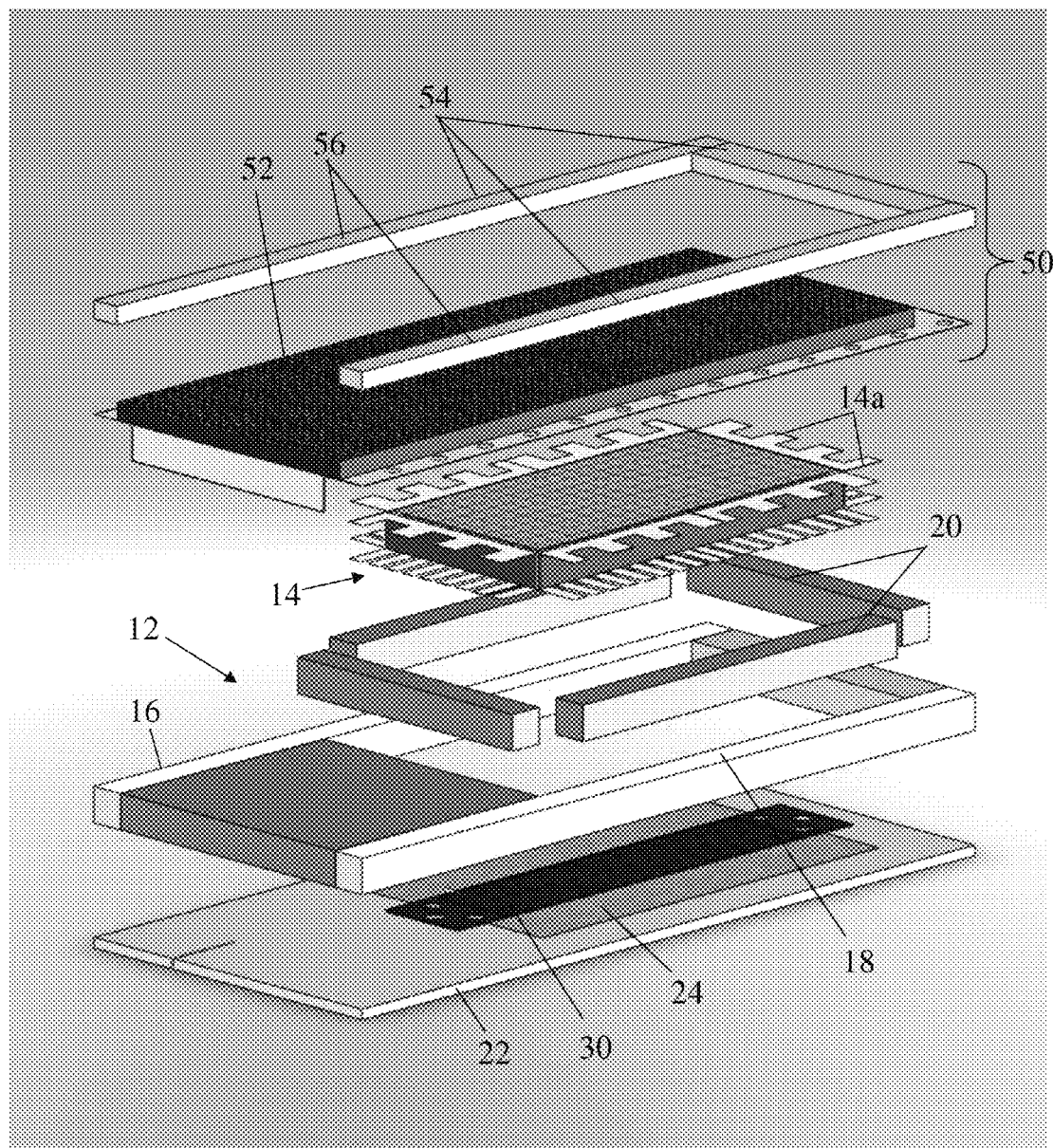
FIG. 2 is an exploded perspective view of a patient support of FIG. 1 with the cover removed.

In the illustrated embodiment, support 10 includes a compressible, resilient layer 12 that is formed by a section of a gel layer 14 and a section of a foam layer 16 (FIG. 2). Foam layer 16 includes a crib 18 to retain gel layer 14 in its location beneath the seat and back regions of the support 10, with the foam layer 16 providing cushioning support to the foot section of the support. As best seen in FIG. 2, crib 18 may include foam inserts 20 to further facilitate retention of gel layer 14 in the crib.

Foam layer 16 is secured to a base foam layer 22, which supports cushioning layer 12 and also gel layer 14. For example, foam layer 16 may be anchored to foam base layer 22 by an adhesive. Layer 22 includes a layer 24 of non-woven material beneath gel layer 14, which is either welded or adhered to the gel layer 14 to provide an interface that can couple to the foam. For example, the non-woven can then be adhered to the foam by way of an adhesive. Similarly, layers of non-woven material may be applied to foam inserts 20 at least on the sides facing gel layer 14, which are then welded to the gel.

In addition to contributing to the overall resiliency of the support, foam layer 16 also provides stability to the gel layer and, further, may be used for line management, e.g. to contain conduits, such as tubing, which may be used to direct fluid, namely air, to the low air loss system described below. Once assembled, the foam layers and gel layer are then enclosed in a fire sock (not shown) and then a cover C (FIG. 1), which may be formed from a moisture vapor permeable, but liquid impermeable material, such as GORE® Medical Fabric, available from W. L. Gore & Associates, Inc., of Elkton, Md. Further, the cover may also be gas or air permeable.

Foam layer 16 may also provide attachment or anchoring surfaces to secure gel layer 14 in the support. In the illustrated embodiment, gel layer 14 is anchored to layer 16 by straps 14a, such nylon straps, which are anchored, such as by an adhesive or VELCRO-like attachments, to foam inserts 20. In addition to securing the gel layer to the support, straps 14a also prevent the gel from collapsing when a patient exits or enters the bed and helps the gel layer return to its original shape. For examples of suitable straps, reference is made herein to U.S. Pat. Nos. 6,843,873 and 6,447,865, which are commonly owned by Stryker Corporation of Kalamazoo, Mich. and which are incorporated by reference herein in their entireties.

As noted above, support 10 is configured to provide a low air loss system that supplies air flow to the patient interface with the support and further without impacting or interfering with the immersion of the patient into the surface of support 10. As best seen in FIG. 2, support 10 includes an air distribution device 30 that has a generally planar arrangement and that may extend along the length of gel layer 14 and across at least partially across the width of gel layer 14. Further, air distribution device 30 is optionally flexible so that it does not interfere with the immersion of the patient into the surface and moreover is not generally detected by an average patient even when fully immersed in the surface or when bottomed out onto the foam base layer 22. In order to minimize detection of the air distribution device 30, the thickness of the air distribution device is in a range of ¼ inch to 2 inches or in a range of ½ inch to 1¾ inches.

Figure 3:
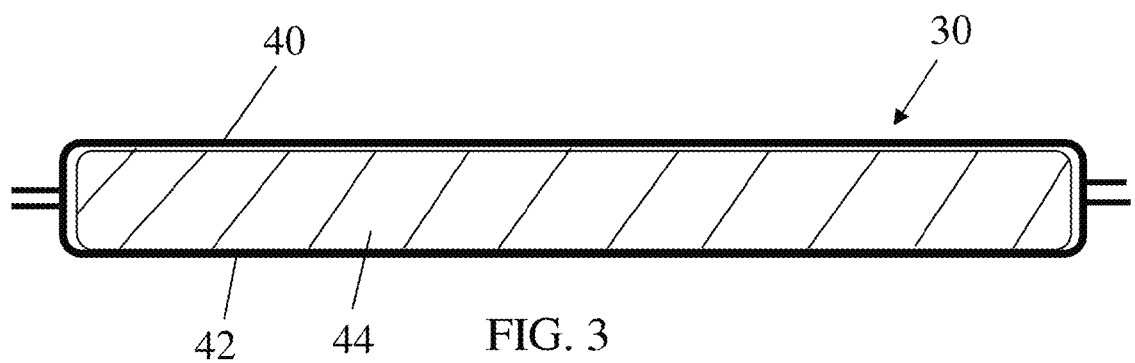
FIG. 3 is a enlarged cross-section view of the air distribution bladder of FIG. 2.

In the illustrated embodiment, air distribution device 30 comprises a bladder and is formed from at least one sheet of material which is folded over and sealed together at or near its unconnected edges to form an upper sheet portion 40 and a bottom or lower sheet portion 42 which define there between an enclosed volume, which forms an air distribution chamber (FIG. 3). For example, the sheet may be sealed by welding, such as by heat sealing, or by gluing. Suitable material for the sheet(s) include non-woven materials, such as nylon, including urethane coated nylon, as well as elastic materials, such as Lycra, including a combination of materials, such as Lycra and GORTEX. It should be understood that bladder 30 may be formed from two or more sheets.

Referring again to FIG. 3, upper sheet portion 40 forms a first or upper first side 40a of the air distribution bladder and includes a plurality of apertures, which either may be formed in the upper sheet portion or may be provided by interstices in the material forming the upper sheet portion. For example, the upper sheet portion 40 may formed from a gas permeable material sheet or may include a region of gas permeable material. Optionally, the upper and lower sheet portions are configured and arranged to maintain a spaced and generally parallel configuration even when the air is flowing into the air distribution bladder. For example, the air distribution bladder may include a porous intermediate, spacer layer 44 that maintains the two sheet portions (and therefore the two sides of the bladder) in their spaced relationship while allowing air to flow through the air distribution bladder. A suitable spacer layer may include a three dimensional (3D) fabric, for example a 3D fabric with a thickness in a range of ⅛ inch to 2 inches, including ¼ inch thick to 1 inch thick. 3D fabrics are woven in three dimensions and may be compressible. Because of their internal structure, 3D fabrics have a plurality of interstices that allow fluid flow, especially air flow both transversely, laterally, and longitudinally through the fabric. Transversely in this context means through the thickness of the fabric. Laterally generally is used in this context to mean through the width, and longitudinally is used in this context to mean through the length of the fabric. Optionally, the two sheet portions may then be connected to the spacer layer, for example by an adhesive. In this manner, even when air is flowing through the air distribution bladder, the bladder can retain its generally flat or planar configuration.

Figure 4:
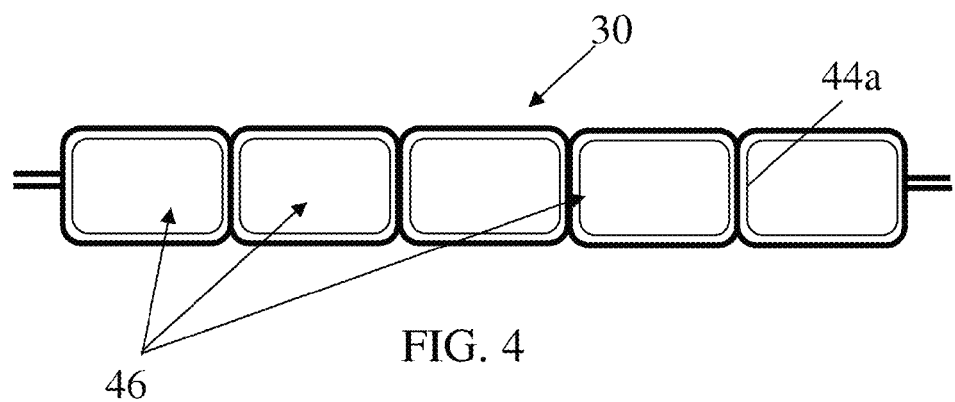
FIG. 4 is a similar view to FIG. 3 of an alternate embodiment of the air distribution bladder.
Figure 5:
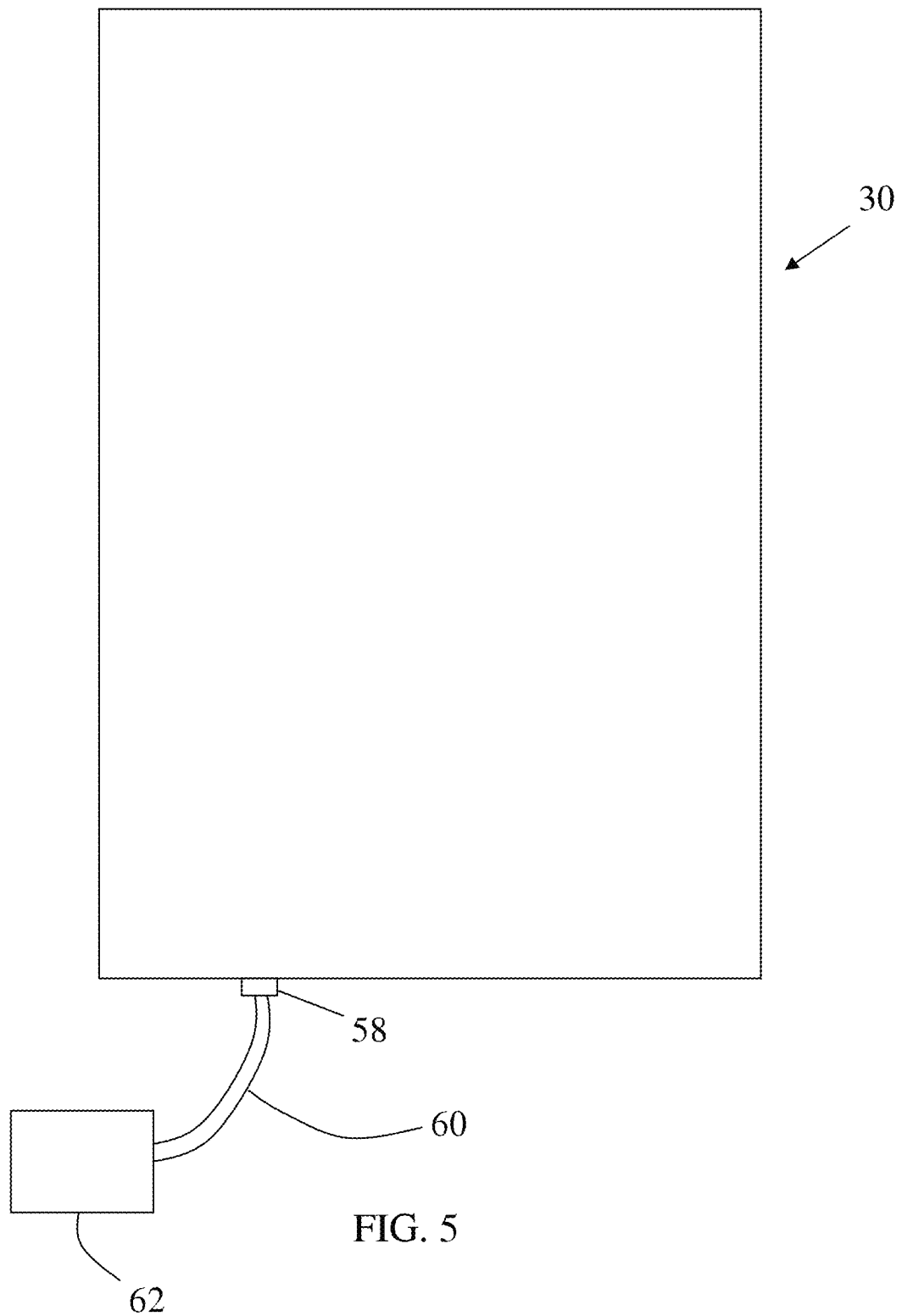
FIG. 5 is schematic drawing of the air distribution bladder and pneumatic system for directing gas to the air distribution bladder.

Alternatively to connecting the sheet portions to the spacer layer, the air distribution bladder's two sheet portions may be interconnected by ties or welds 46 in a plurality of locations across the air distribution bladder so that the air distribution bladder remains generally flat when inflated (FIG. 4). These connections may be extended through the spacer fabric (for example through openings 44a), or they may simply fuse the sheets and the spacer fabric together.

When inflated, therefore, the variation in thickness of the air distribution bladder may be essentially zero or may vary in a range of ¼ inch to 2 inches or in a range of ½ inch to 1¾ inches depending on the overall thickness of the bladder. Further, the variation in thickness when inflated may be less than ½ inch or less than ¼ inch, and optionally less than ⅛ inch.

In yet another embodiment, the air distribution bladders may be formed from a semi-rigid material, such as a corrugated panel, with the corrugations forming air flow passageways through the bladder. Again, openings may be provided in the upper side of the air distribution bladder, which are in fluid communication with the passageways to allow the air distribution bladders to direct air flow to the patient interface with the cushion layer. In this manner, the spacer material may be eliminated.

While only one air distribution bladder is illustrated, it should be understood that two or more air distribution bladders may be used. Further, the width and length of the bladder or bladders may be increased or decreased so that the bladder can extend across the full width of the gel layer or only partially across the length of the gel layer.

Referring again to FIG. 2, air distribution bladder 30 is located on top of non-woven layer 24 and further anchored to the foam base layer 22. For example, one or both ends of the air distribution bladder 30 may be anchored, such as by welding or by an adhesive, to foam layer 22.

In addition, support 10 may include a second cushioning layer 50. Cushioning layer 50 may also include a section of gel layer 52 and a U-shaped section of foam 54, which forms foam side bolsters 56. Gel layer 52 forms a topper and extends from the head end of the support to the foot end and is flanked by the foam bolsters, which provides stability to the gel layer and, further, provides a firm edge for the support to ease ingress and egress for a patient. In addition, because of the firmness difference between the gel and the foam, the gel layers will tend to compress more than the bolsters, so that the bolsters form a barrier to cradle the patient in the support, which reduces the chances of a patient falling off the bed on which the mattress is supported. Optionally, the foam bolsters may be taller than gel layer 52 to form an even taller barrier. Gel layer 52 may also include flanges 52a that extend along its length and/or width, which are formed from a fabric and which are adhered to the foam side bolsters 56 and sandwiched between side bolsters 56 and foam inserts 20 to thereby anchor the gel layer in the surface. Optionally, the end flange may be anchored, for example by an adhesive, to the foam crib below.

Gel layers 14 and 50 are both formed with transverse openings that extend through the respective layers so that air flowing from air distribution bladder 30 can flow to the interface between the patient and the support at or near the upper surface of gel layer 50. Although illustrated as being beneath gel layer 14, air distribution bladder 30 may be located between the gel layers. In this configuration, the air distribution bladder 30 could be anchored to the straps, for example.

Suitable gelatinous elastomeric materials for forming the gel layers may be formed by blending an A-B-A triblock copolymer with a plasticizer oil, such as mineral oil. The "A" component in the A-B-A triblock copolymer is a crystalline polymer like polystyrene and the "B" component is an elastomer polymer like poly(ethylene-propylene) to form a SEPS polymer, a poly (ethylene-butadyene) to form a SEBS polymer, or hydrogenated poly(isoprene+butadiene) to form a SEEPS polymer. For examples of suitable gelatinous elastomeric materials, the method of making the same, and various suitable configurations for the gel layer reference is made to U.S. Pat. Nos. 3,485,787; 3,676,387; 3,827,999; 4,259,540; 4,351,913; 4,369,284; 4,618,213; 5,262,468; 5,508,334; 5,239,723; 5,475,890; 5,334,646; 5,336,708; 4,432,607; 4,492,428; 4,497,538; 4,509,821; 4,709,982; 4,716,183; 4,798,853; 4,942,270; 5,149,736; 5,331,036; 5,881,409; 5,994,450; 5,749,111; 6,026,527; 6,197,099; 6,843,873; 6,865,759; 7,060,213; 6,413,458; 7,730,566; 7,823,233; 7,827,636; 7,823,234; and 7,964,664, which are all incorporated herein by reference in their entireties.

Other formulations of gelatinous elastomeric materials may also be used in addition to those identified in these patents. As one example, the gelatinous elastomeric material may be formulated with a weight ratio of oil to polymer of approximately 3.1 to 1. The polymer may be Kraton 1830 available from Kraton Polymers, which has a place of business in Houston, Tex., or it may be another suitable polymer. The oil may be mineral oil, or another suitable oil. One or more stabilizers may also be added. Additional ingredients—such as, but not limited to—dye may also be added. In another example, the gelatinous elastomeric material may be formulated with a weight ratio of oil to copolymers of approximately 2.6 to 1. The copolymers may be Septon 4055 and 4044 which are available from Kuraray America, Inc., which has a place of business in Houston, Tex., or it may be other copolymers. If Septon 4055 and 4044 are used, the weight ratio may be approximately 2.3 to 1 of Septon 4055 to Septon 4044. The oil may be mineral oil and one or more stabilizers may also be used. Additional ingredients—such as, but not limited to—dye may also be added. In addition to these two examples, as well as those disclosed in the aforementioned patents, still other formulations may be used.

Air distribution bladder 30 may be filled with air by an external air supply or an air supply built into the support. For example, bladder 30 may include one or more inlets 58 that couple to tubing 60 that extends from the bladder to beneath foam base layer to connect to an air flow device, such as pump or a fan, which is then regulated by a conventional control. The pump and any supporting control system may be mounted in the support itself, such as described in U.S. Pat. Nos. 5,325,551, and 5,542,136, both commonly owned by Stryker Corporation of Kalamazoo, Mich., or may be located external to the support, for example at the footboard or the side rail, or at other locations on or off the bed. Air may be pushed or pulled through the bladder. Further, the air flow may be bidirectional. As is understood, pulling air meets with less resistance than pushing air so pulling air may be preferred in order to reduce the size of the air flow device. The air may be cool air, ambient air, or warmed air. For example, a Peltier device, which can provide cold or warm air, may be incorporated into the air supply system to allow the air to be cooled or warmed as desired.

In addition, at least the case of the corrugated distribution bladder, a manifold may be mounted to the end of the corrugated panel, which then couples to the tubing to distribute air to each of the channels formed by the corrugations.

In another embodiment, the patient support may include a layer of air support bladders in lieu of the gel layers as the cushion layer. The bladders each have an upwardly facing surface for facing and supporting the patient. The layer of bladders also includes transverse openings that extend through the layer of bladders from the lower side of the layer to the patient facing side of the layer. For examples of suitable air support bladders that form a cushioning layer reference is made to U.S. pending patent application Ser. No. 12/640,770 filed Dec. 17, 2009, entitled PATIENT SUPPORT; Ser. No. 12/640,643 filed Dec. 17, 2009, entitled PATIENT SUPPORT; Ser. No. 13/022,326 filed Feb. 7, 2011, entitled PATIENT/INVALID HANDLING SUPPORT; Ser. No. 13/022,372 filed Feb. 7, 2011, entitled PATIENT/INVALID HANDLING SUPPORT; Ser. No. 13/022,382 filed Feb. 7, 2011, entitled PATIENT/INVALID HANDLING SUPPORT; and Ser. No. 13/022,454 filed Feb. 7, 2011, entitled PATIENT/INVALID HANDLING SUPPORT, all commonly owned by Stryker Corporation of Kalamazoo, Mich., which are herein incorporated by reference in their entireties. The air distribution bladder can then located below the air support bladders to direct air flow through the layer of air support bladders.

While several forms of the invention have been shown and described, other changes and modifications will be appreciated by those skilled in the relevant art. Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

The embodiments of the invention in which we claim an exclusive property right or privilege are defined as follows:

1. A patient support comprising:
    a mattress having an upper side forming a patient support surface, the mattress including an internal gel cushioning layer having a plurality of gel walls defining first and second spaced apart sides, the first side facing in the direction of the patient support surface and being recessed below the patient support surface, the gel walls forming-transverse passageways extending from the first side to the second side through the gel-cushioning layer;
    the mattress including a second cushioning layer over the gel cushioning layer;
    a flexible air distribution manifold located beneath the second side of the gel cushioning layer, the transverse passageways allowing airflow flowing from the air distribution manifold to flow into the second side, through the gel cushioning layer, and from the first side of the gel cushioning layer toward the second cushioning layer; and
    wherein the gel cushioning layer comprises a first gel cushioning layer, the second cushioning layer comprising a second gel cushion layer extending over the first gel cushioning layer and having a greater width or length than the first gel cushioning layer.

2. The patient support according to claim 1, wherein said air distribution manifold comprises a bladder with a first side and a second side spaced from and generally parallel to the first side wherein the bladder has a generally flat or planar configuration.

3. The support according to claim 2, wherein the first and second sides of the air distribution bladder remains in its spaced and generally parallel configuration even when the air distribution bladder is fully inflated.

4. The support according to claim 2, wherein the air distribution bladder includes a porous intermediate spacer layer, said porous intermediate spacer layer maintaining the two sides in their spaced relationship while allowing air to flow through the air distribution bladder.

5. The support according to claim 4, wherein the spacer layer comprises a three dimensional fabric.

6. The support according to claim 2, wherein the air distribution bladder includes a plurality of ties or welds in a plurality of locations across the air distribution bladder to maintain the two sides in the spaced relationship.

7. The support according to claim 2, wherein the air distribution bladder has a thickness in a range of ¼ inch to 2 inches.

8. The support according to claim 2, wherein the air distribution bladder is formed from at least one sheet of material, the at least one sheet forming an upper sheet portion and a lower sheet portion, the upper sheet portion including a plurality of apertures therethrough to allow airflow in the air distribution bladder to flow through the upper sheet portion.

9. The support according to claim 8, wherein the apertures comprise interstices in the material forming at least a part of the upper sheet portion.

10. The support according to claim 9, wherein the upper sheet portion comprises at least a region of a gas permeable sheet.

11. The patient support according to claim 1, further comprising a foam cushioning layer with a recess, said air distribution manifold located beneath said foam cushioning layer, and said first gel cushioning layer located in said recess.

12. The support according to claim 1, wherein the distribution manifold extends across the full width or full length of the first gel cushioning layer.

13. The support according to claim 1, further comprising a foam crib, the foam crib supporting the gel cushioning layers, and the air distribution manifold being located beneath the foam crib.

14. The patient support according to claim 1, wherein the gel walls form hollow gel supports.

15. The patient support according to claim 14, wherein the gel walls comprise a first group of gel walls and a second group of gel walls, the first and second groups of gel walls intersecting to form the hollow gel supports.

16. The patient support according to claim 15, wherein the first group of gel walls is orthogonal to the second group of gel walls.

\* \* \* \* \*